United States Patent [19]

Mears

[11] Patent Number: 6,113,614
[45] Date of Patent: Sep. 5, 2000

[54] MEDICAL DEVICE FOR DISSOLUTION OF TISSUE WITHIN THE HUMAN BODY

[75] Inventor: Eric L. Mears, Duluth, Ga.

[73] Assignee: EnSurg, Inc., Norcross, Ga.

[21] Appl. No.: 09/073,227

[22] Filed: May 5, 1998

[51] Int. Cl.[7] .................................................. A61B 17/00
[52] U.S. Cl. .......................................... 606/159; 606/170
[58] Field of Search ............................... 606/1, 108, 159, 606/170, 180, 194; 15/72, 104.14

[56] References Cited

U.S. PATENT DOCUMENTS

| | | | |
|---|---|---|---|
| 4,646,736 | 3/1987 | Auth . | |
| 4,772,258 | 9/1988 | Marangoni et al. . | |
| 5,009,659 | 4/1991 | Hamlin et al. | 606/159 |
| 5,041,124 | 8/1991 | Kensey | 606/170 |
| 5,170,805 | 12/1992 | Kensey et al. | 606/159 |
| 5,370,653 | 12/1994 | Cragg | 606/170 |
| 5,681,335 | 10/1997 | Serra et al. | 606/159 |

FOREIGN PATENT DOCUMENTS

| | | |
|---|---|---|
| WO 94/13217 | 6/1994 | WIPO . |
| WO 96/19148 | 6/1996 | WIPO . |
| WO 98/38926 | 9/1998 | WIPO . |

*Primary Examiner*—Michael Buiz
*Assistant Examiner*—William Lewis
*Attorney, Agent, or Firm*—Sidley & Austin

[57] ABSTRACT

A device for dissolving friable or coagulated tissue within a human body is provided, such lysing operation being achieved through high-speed rotation of at least one thread- or ribbon-like lysing member. Lysing is achieved through shear and/or wear. A flexible drive member, used to rotate the at least one lysing member, may be received within an encompassing, static flexible member. Interaction between the rotating flexible drive member and the encompassing static flexible member causes at least lysed tissue to be pumped and further dissolved along the encompassed length of the flexible drive member.

56 Claims, 2 Drawing Sheets

MEDICAL DEVICE FOR DISSOLUTION OF TISSUE WITHIN THE HUMAN BODY

FIELD OF THE INVENTION

The present invention relates to a medical device to dissolve friable or coagulated tissue within the environment of the human body, and in particular, to a medical device to dissolve friable or coagulated tissue through shear and/or wear as well as remove solid/semi-solid tissue from the dissolution site.

BACKGROUND OF THE INVENTION

A variety of medical devices are known to facilitate the physical destruction and removal of obstructive tissue (e.g., vascular plaque and thrombotic occlusions) or living tissue (e.g., the lining of a Fallopian tube for purposes of sterilization). A class of these devices include a motor, for providing a rotary drive, a cutting tip, and a drive shaft spanning therebetween.

The cutting tip of known devices commonly features a rigid or semi-rigid cutting portion. The cutting portion is used to destroy tissue positioned distal to the device. In addition to, or as an alternative, known devices may also incorporate whips or fibers positioned about a longitudinal, outer periphery of the device. The whips and fibers are intended to engage tissue which surrounds the longitudinal outer periphery of the device. Commonly, the cutting portions, whips, and fibers are constructed of a material sufficient to destroy friable and coagulated tissue as well as surrounding living tissue.

With regard to those devices having rotating or moving whips/fibers, the whips/fibers are commonly predisposed in a substantially normal orientation relative to the device, or they are caused to assume such orientation through the rotation of the device. Known devices of this nature include stiff bristles rotated at slow speeds to gather cell samples or to permanently entangle a thrombus. These devices have particular application in removing deposits or tissue surrounding the diametrical periphery of the bristles but have little use in engaging material or tissue positioned distal to the device.

Rigid or semi-rigid cutting portions which are intended to engage material or tissue positioned distal to the cutting portion traditionally include aggressive rotating prongs, drill tips, or blade-like elements. For these devices, a user must precisely control the longitudinal movement of the device to achieve a desired depth of cut and avoid damage to surrounding tissue; however, because known devices tend to obstruct the view of the operator, if any, when in use, the necessary degree of control may be unachievable. Further, the cutting portions of these conventional devices do not include that which would prevent the destruction of living tissue, i.e., the cutting surfaces are equally suited to engage and destroy living tissue as well as other tissue or material (for example, blood deposits, thrombi, plaque, and the like). Guards, baskets, or shields can be incorporated to protect viable tissue from destructive cutters; however, visibility, compactness, and the effectiveness of the device can be compromised. Moreover, failure of a tissue protecting guard may precipitate the infliction of instant and severe trauma.

Consequently, a need exists for an intrinsically safe medical device permitting distally-positioned friable or coagulated tissue to be confronted and lysed, or dissolved, while avoiding the destruction of surrounding tissue or material. A further need exists for a device having at least one flexible member, such member generating a lysing zone which conforms to its operating environment and, when used with an endoscope, is transparent, planar, and normal to the distal tip of an endoscope to enable direct visualization of both targeted and surrounding tissue. Even with a device to satisfy these needs, a further need exists for a device capable of forcibly removing fluid as well as partially lysed tissue (including tissue particles) from the lysing site.

A device consistent with the above needs would have a plurality of applications. As an example, an uncleared fundal pool of retained blood in a stomach can preclude complete visualization of the stomach interior during endoscopic evaluation. In cases of acute upper gastrointestinal bleeding, the inability to clear a fundal pool of clotted blood in the stomach at the time of emergent upper endoscopy can result in patient morbidity and mortality. Accordingly, a need exists for a device to clear a stomach fundus of blood and other fluids and materials in patients undergoing urgent endoscopy for acute upper gastrointestinal bleeding.

As another application example, thrombotic occlusions can result in myocardial infarctions (i.e., coronary occlusions) and strokes (i.e, cerebral occlusions). While in an emergency or in an instance that such occlusions cannot readily be treated with drugs, a need remains for a device to allow such thrombotic occlusions to be rapidly and safely removed without traumatizing the surrounding tissue.

With regard to the removal of solid and semi-solid tissue following lysing, atherectomy cutters and other devices designed to remove obstructive tissues such as a thrombus, an embolism, or a massive clot in the stomach, tend to produce liquid plus a range of resultant tissue particles, including some that are large. Conventional suction of this mixture for removal and subsequent transport is frequently impossible when these particles clog a conventional, small-bore suction catheter or an endoscope working channel.

While conventional techniques include rotation of a patterned shaft within the bore of the suction catheters, this technique is susceptible to entrapping smaller tissue particles and obstructing the path of the suction catheter. In this instance, the trapped tissue merely rotates along the interior surface of the suction catheter but does not displace axially, thus preventing the transport of either tissue particles or fluid from the bodily region. Moreover, this assembly may prevent the admission and transport of larger tissue particles.

SUMMARY OF THE INVENTION

The present invention is directed to a mechanical device for physically dissolving friable or coagulated material within a human body. According to one aspect of the present invention, the device includes a drive member having a proximal end and a distal end. While the proximal end is adapted to engage a rotary drive source, the distal end has a filament member which extends distally therefrom when the flexible member is rotated at a speed at least equal to a predetermined rotational speed. The thread member is suited to dissolve friable/coagulated material distally positioned from drive member when the flexible member is rotated at the predetermined rotational speed and above.

In another embodiment, a second flexible member is provided which encompasses at least a portion of the drive member. A proximal end of the second flexible member is suitable to be coupled to a suction device. In addition to the suction provided by the suction device when operative, a dynamic interaction between the drive member and the second member causes fluid and material to be forcibly drawn and transported proximally through an annular passage formed between the first member and the second member.

For another embodiment of the present invention, a lysing device for physically dissolving friable/coagulated material within a vessel and transporting the dissolved material away from the dissolution site is provided. The device has a first coil member having a proximal end and a distal end, the proximal end being adapted to engage a rotary drive source and the distal end having a filament member extending therefrom. The filament member has a length and is suitable to lyse friable/coagulated material positioned distally to the lysing device when the first coil member is rotated at least at a predetermined rotational speed. An encompassing second coil interacts with the first coil to transport lysed matter proximally while further dissolving the transported matter.

An object of the present invention is to overcome the limitations of those devices and instruments currently known so as to enable the performance of desired medical procedures.

Another object of the present invention is to provide a mechanical device for dissolving friable or coagulated material within the human body, wherein the device can be positioned within, for example, a biopsy channel of a conventional endoscope. Moreover, this object further includes the ability to position the present invention after the insertion vehicle is positioned within the patient, thus minimizing patient discomfort, risk, and the time necessary to prepare the insertion device prior to placement within a patient.

Another object of the present invention is to provide a mechanical device for dissolving friable or coagulated tissue within the human body, where when such device is positioned within a biopsy channel of a conventional endoscope and operated, the device does not obstruct the field of view of the image sensing device of the hosting endoscope but allows full visibility of the dissolving zone in real time.

Another object of the present invention is to provide an intrinsically safe mechanical device for lysing friable or coagulated material within the human body, wherein a lysing member is suitable for dissolving engaged friable or coagulated material through shear and/or wear but is ill-suited for destroying surrounding living tissue.

Another object of the present invention is to provide a mechanical device for lysing plaque-like material on the walls of vessels within the human body.

Another object of the present invention is to provide an embodiment of the mechanical device for dissolving friable or coagulated tissue within a vessel, wherein a lysing member automatically conforms during operation to an inner diameter of the vessel.

Another object of the present invention is to provide a mechanical device for the reliable removal and transport of lysed tissue particles and which further resists clogging.

Other objects and advantages of the present invention will be apparent to those of ordinary skill in the art having reference to the following Specification together with the drawings.

BRIEF DESCRIPTION OF THE DRAWINGS

Referring now to the drawings in which like reference numerals and letters indicate corresponding elements throughout the several views, if applicable.

DETAILED DESCRIPTION OF THE PREFERRED EMBODIMENTS

Figure 1:
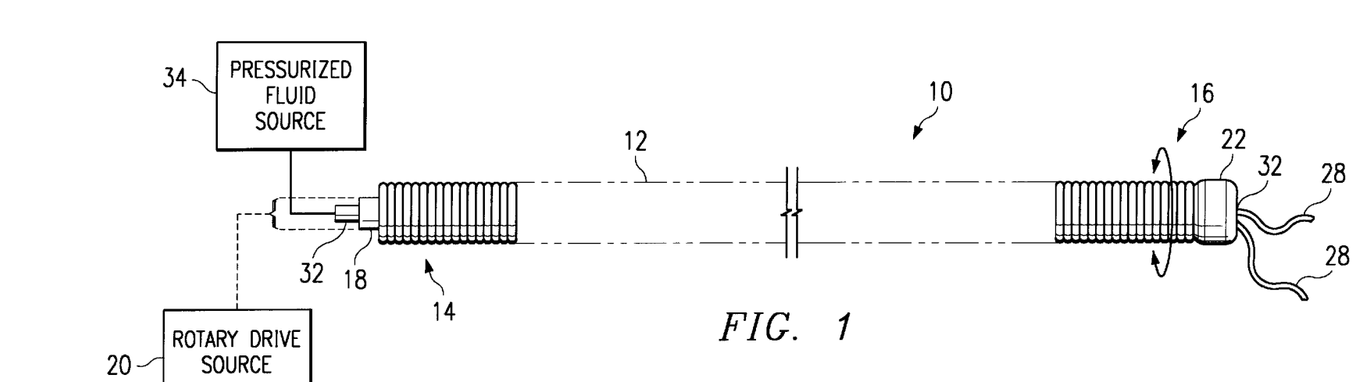
FIG. 1 is a mechanical device in accordance with a first embodiment of the present invention.

FIG. 1 illustrates one embodiment of mechanical device 10 in accordance with the present invention. Mechanical device 10 includes flexible coil member 12 having a proximal end 14 and a distal end 16. Coil member 12 is formed of a medical grade material, for example, stainless steel, nitinol, or a plastic composition. Coil member 12 may have a variable length, such length being dependent upon the nature of the procedures to be performed. If device 10 is intended to be used with an endoscope (not shown), coil member 12 shall have a length sufficient to properly extend for the length of a flexible portion of the endoscope. Coil member 12 allows extreme flexibility along its length, thus enabling device 10 to follow and assume that distortion necessary to follow tortuous paths defined by guides (for example, endoscopes, insertion catheters, or guide wires) and/or the human body. While the illustrated embodiments of coil member 12 are shown having a close-coil configuration, an alternative construction for coil member 10 (or second member 36, as will be discussed in greater detail below) includes a spaced-coil configuration, having fixed or variable pitch, to optimize performance characteristics such as flexibility, tissue transport, or torsional strength.

Fixed within the proximal end 14, mounting collar 18 is provided to engage rotary drive source 20. Rotary drive source 20 may include an electric motor or an air-driven motor. In a preferred embodiment, rotary drive source 20 is a variable speed DC motor, capable of normally producing operational rotational speeds of 500 to more than 50,000 RPM.

Figures 2, 3:
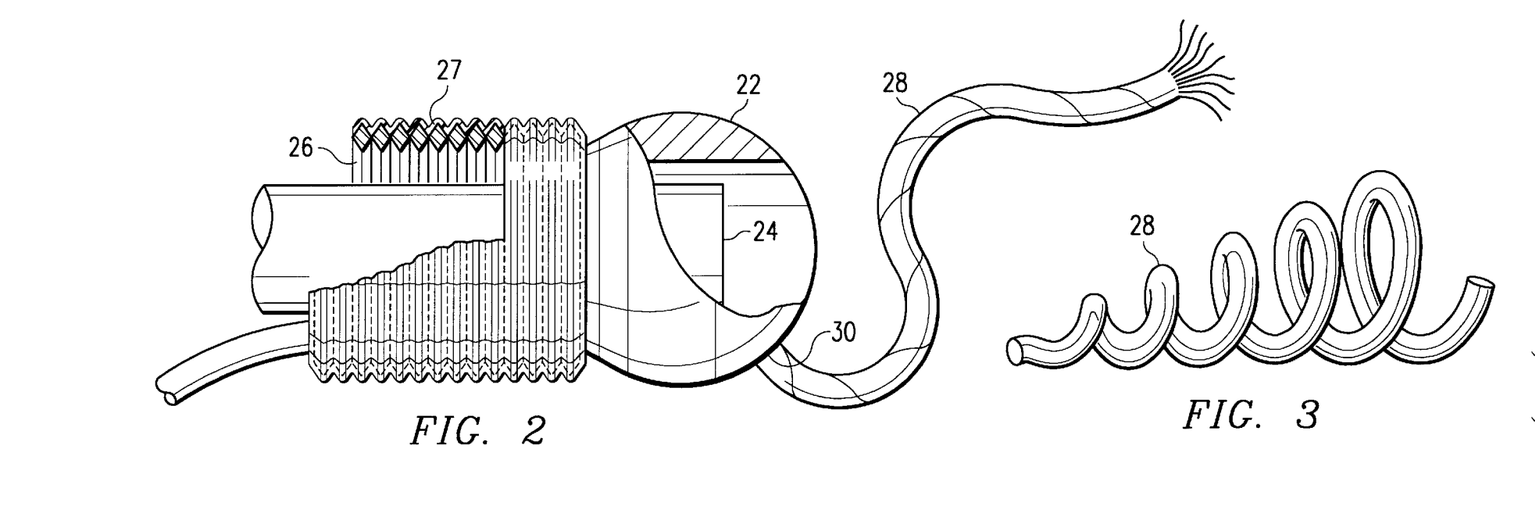
FIG. 2 is a partial sectional view of a distal end portion of a mechanical device in accordance with another embodiment of the present invention.
FIG. 3 is a perspective view of an alternative lysing member for the present invention.

Tip 22 is provided at distal end 16 of coil member 12. Tip 22 may be integrally formed with, frictionally engage, or joined (for example, using an adhesive, a weld, or the like) to coil member 12. Tip 22 may assume a conventional configuration and comprise any of a plurality of known rigid or semi-rigid cutting portions or known whip/fiber portions, as discussed above. In a preferred embodiment, however, tip 22 generally assumes a blunt form. Tip 22 serves to protect soft, internal tissue from the distal end 16 of coil member 12. As shown in FIG. 2, passage 24 may extend through tip 22. Passage 24 is axially aligned with a generally longitudinal passage 26 of coil member 12. Tip may be alternatively solid or integrally formed of coiled wire (not shown).

Figure 4:
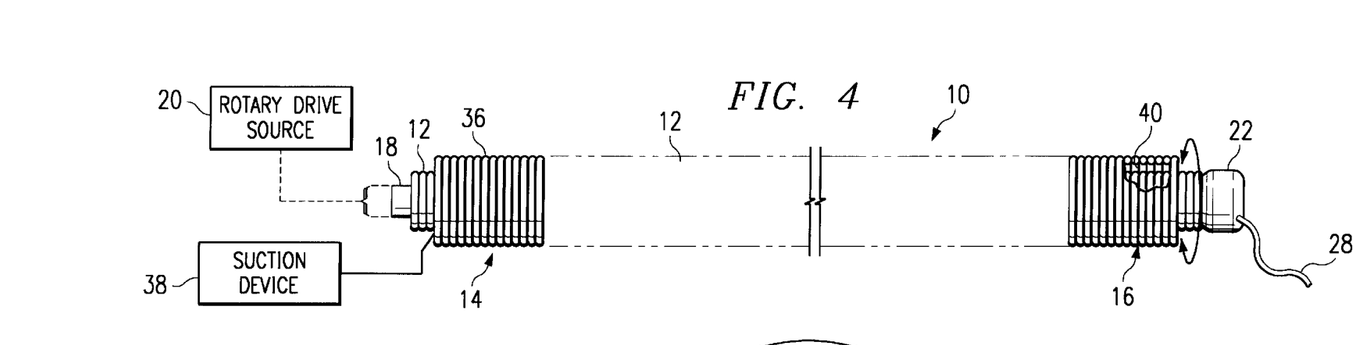
FIG. 4 is a partial sectional view of a mechanical device in accordance with another embodiment of the present invention.

For this preferred embodiment, extending from tip 22 are one or more members 28. Members 28 may be monofilaments (FIG. 1), stranded filaments (FIG. 2), or a tape-like member (FIG. 4). Alternative forms for member 28 could include flexible pre-formed shapes, for example, a thin-member, tapered helix formed from a plastic material or a coated filament (FIG. 3), the coating being applied so that the stiffness of the filament decreases distally. For the latter configuration, the coating material could be of such a nature as to dissolve or the like to enable operational behavior consistent with non-coated filament members 28. Operationally, the tapered helix members 28 could be operated at low rotational speeds to spirally penetrate material/tissue to be dissolved, and then the rotational speed increased to enable the dissolution of the penetrated material/tissue.

For the preferred embodiment, members 28 are formed from a high density, fibrous material, for example, oriented, expanded polytetrafluoroethylene (PTFE) thread or Teflon® filament. Members 28, such as those shown in FIGS. 1 and 2, have a diameter of between approximately 0.025 mm and 0.510 mm.

Rotated members 28 create a largely planar dissolving zone having a diameter of up to two times the length of members 28 and a depth as little as the width of members 28. In operation, the high-speed rotation of members 28 shear fluid-based material or coagulated tissue to create a thin, planar zone of vortex-like turbulence. The shearing of members 28 as well as such turbulence cause the substantive material of fluid-based material or coagulated tissue to be torn apart and, effectively, dissolved.

Members 28 may also be formed with or later receive certain abrasive material, for example, microscopic diamond or sapphire crystals. These embodiments enable members 28 to dissolve tissue/material responsive to abrasive removal, for example, calcified arterial plaque, during rotation.

Members 28 are positioned relative to tip 22 (on a distal face) so that when coil member 12 is rotated, distal ends of members 28 extend beyond tip 22. The lithe nature of members 28, coupled with the drag of high-speed rotational contact with the tissue being dissolved as well as the positioning of members 28 relative to tip 22, prevents members 28 from assuming a substantially normal orientation relative to coil member 12 when coil member 12 is rotated. Instead, as a function of their flexibility and length for at least one embodiment, members 28 assume a generally spiral shape about a longitudinal axis of coil member 12, thus creating a vortex-inducing path through the material/tissue being dissolved and/or allowing a greater proportion of the length of members 28 to come in contact with tissue/material to be dissolved.

The effective diameter of the spiral geometry of members 28 can be established by the operating environment as well as the operational parameters of device 10. "Operational parameters" may include the composition of the dissolving material; feed rate of tip 22 into the tissue; length, composition, and number of members 28; and the rotational speed of device 10. For vascular-type environments, for example, the maximum rotational diameter assumed by members 28 is defined by an inner vessel diameter; provided, however, the inner vessel diameter is equal to or less than two times the length of members 28.

While FIGS. 1 and 4 illustrate members 28 being fixed to preferred tip 22, FIG. 2 illustrates an alternative embodiment. Member 28 passes through aperture 30 in tip 22 and extends proximally to proximal end 14. For this embodiment, member 28 may be extended and retracted during the course of insertion, conducting a procedure, or withdrawal in accordance with the desires of a user. To facilitate extension and withdrawal, members 28 may be provided with a rigid portion (not shown) at the proximal end 14 which may extend for a length distally.

In reference to FIGS. 1 and 2, tubing 32 is provided to deliver fluid, for example, pressurized air, water or saline, or a tissue dissolving fluid to distal end 16. A proximal end of tubing 32 is coupled to pressurized fluid source 34, and a distal end of tubing 32 extends into passage 24 formed in tip 22. It is preferred that tubing 32 remain substantially static relative to the rotation of coil member 12; however, in at least one embodiment, tubing 32 rotates with coil 12 and may also be constructed integral with coil 12.

Figure 6:
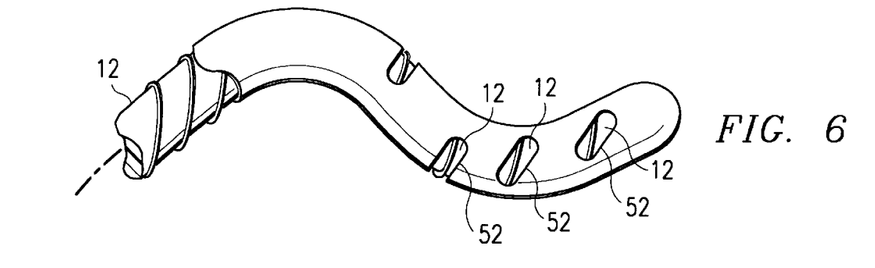
FIG. 6 illustrates an application of another embodiment of the mechanical device of the present invention.

FIG. 4 illustrates another embodiment of the present invention. While device 10 maintains structure similar to that described above, device 10 of this embodiment further includes second member 36. Second member 36 is shown as a coil similar to that of coil member 12 and may include a thin, fluid impermeable sheath or membrane encompassing its outer surface. As shown in FIG. 6, second member 36 may alternatively take the form of tubing or the like having characteristics in accordance with the features and functionality discussed below.

A distal end of second member 36 is positioned at or about distal end 16. A proximal end of second member 36 is coupled to suction device 38. Operatively, it is preferred that second member 36 remain substantially static relative to the rotation of coil member 12.

Second member 36 has an inner diameter substantially equal to or slightly greater than the outer diameter of coil member 12. Accordingly, annular channel 40 is formed between coil member 12 and second member 36. Rotation of coil member 12 in a direction consistent with the winding of coil member 12 facilitates fluid and tissue particles to be drawn into channel 40 at distal end 16 and moved proximally to proximal end 14. In the preferred embodiment, the proximal movement of fluid and tissue is enhanced through second member 36 having a winding in a direction opposite of that of coil member 12. Where second member 36 is tubing, one or more helical or axial ridges 37 (FIG. 7) may be formed within the bore of second member 36, for example, a helical groove spirals in a direction opposite to the winding of coil member 12.

Through rotation of coil member 12, the outer diameter of coil member 12 comes in contact with the inner diameter of second member 36. At greater rotational speeds, such contact produces strong pressure pulses which facilitate the proximal movement of fluid and tissue particles within channel 40. These pressure pulsations also serve to actively and aggressively dislodge any tissue which may tend to clog channel 40. Moreover, the contact of individual coils of coil member 12 with individual coils (or groove surfaces) of second member 36 introduces a scissor-like, shear action in a direction traverse to the longitudinal direction of channel 40. Consequently, this shear effect serves to further dissolve that tissue/material drawn into channel 40.

To further increase the drawing effect as well as shearing consequence of coil member 12 and second member 36, the individual coils could take specialized cross-sectional shapes. Specifically, in addition to common circular or elliptical cross-sections (FIG. 4), other embodiments could feature diamond cross-sections (FIG. 2) or trapezoidal cross-sections (not shown).

Fluid and tissue which is drawn proximally through channel 40 may be carried away from device 10 using suction device 38. In addition to merely removing that fluid/material carried proximally through the relationship of coil member 12 and second member 36, suction device 38 may communicate a drawing force distally along the length of channel 40 to augment the interactive pumping action of members 12, 36.

Tubing 32 may be modified for device 10 of FIG. 4 to further its material/tissue removing operations. Whether tip 22 is provided with passage 24 (FIGS. 1 and 2) or not, it is preferred that tubing 32 include one or more orifices (not shown) along its longitudinal length to dispense fluid, pressurized or otherwise, for the purpose of preventing blockages from forming, or clearing blockages which do form, in channel 40. As coil member 12 is preferably an open, spiral of material, coil member 12 is readily capable of passing fluid which has been delivered therein, outward into channel 40.

Discussing exemplary applications of the various embodiments of device 10 set forth above, the following discussion will focus, in turn, on device 10 being used with a suction/irrigation tube, as a flexible drainage tube, as a fundal blood pool evacuation device, and as a thrombotic occlusion removal device. While these applications are examples of possible use, one skilled in the art will appreciate that further applications exist which would benefit from the unique features of the present invention.

Figure 5:
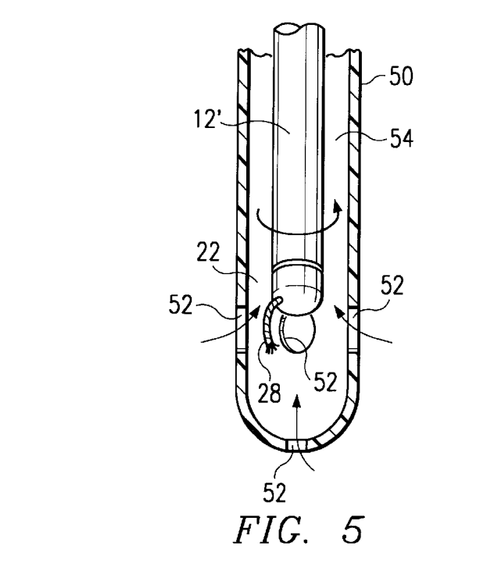
FIG. 5 illustrates an application of one embodiment of the mechanical device of the present invention.

In reference to FIG. 5, device 10 having a semi-rigid shaft 12', for example, a conventional guide wire, is positioned within that portion of a suction/irrigation tube 50 which is inserted within a patient, for example, during surgery. Without device 10, suction of fluids and tissue material can result in the obstruction of inlets 52 and/or the central passage 54. In contrast, operation of device 10 within the suction/irrigation tube clears and/or prevents the formation of obstructions through shear and/or wear.

Depending upon the application, shaft 12' may be rigid. While shaft 12' may intrinsically possess an outer surface with a pattern (e.g., a guide wire), ridges and/or protrusions may be used to form a helical path about shaft 12' to facilitate functionality consistent with coil member 12.

In reference to FIG. 6, one aspect of the present invention is incorporated within a drainage tube, catheter, or stent. In particular, a flexible coil-like member 12 is positioned within perforated, blind tubular catheter or stent casing 36, where catheter 36 has internal ridges or protrusions along its inner diameter (not shown). Perforations 52 may be round, oval, spiral, or of another shape to optimize flow, safety, and tissue entry. Perforations 52 may be provided at the distal end of catheter 36 or along the body of catheter 36 for a prescribed distance. For this embodiment, tip 22 with member 28 is optional.

Catheter 36 may be inserted, for example, into a bladder or general surgical site, in a convention manner with or without member 12. Should a blockage occur which reduces drainage or fluid flow from catheter 36, member 12 may be inserted (if not already so) and rotated to clear catheter 36 or perforations 52. As member 12 may be employed on a need only basis, patients are spared the discomfort of catheter replacements or the cost of employing this device unnecessarily.

As a stomach fundal blood pool dissolution and evacuation device, device 10 is used in conjunction with a conventional endoscope (not shown). Specifically, coil member 12 is inserted through the biopsy channel of a hosting endoscope. It is preferred that device 10 be capable of insertion through the biopsy channel even after the flexible portion of the endoscope, i.e., that portion in which the biopsy channel passes, is already positioned within the body of a patient. Consequently, the greatest diameter of tip 22 and coil member 12 (FIG. 1) or second member 36 (FIG. 4) is less than approximately 2.8 mm.

While device 10 with second member 36 may be scaled to fit within an endoscope biopsy channel, device 10 without second member 36 may also be used. In such instance, the inner diameter of the biopsy channel will function as a smooth-bore second member 36. For purposes of the following discussion, however, device 10 will assume the characteristics of FIG. 4 but having a thread-like member 28.

In the event of acute upper gastrointestinal bleeding, a pool of blood and clotted blood will accumulate in the fundus of the stomach. An uncleared fundal pool of retained blood can preclude complete visualization of the stomach interior during endoscopic evaluation. Moreover, the solid and semi-solid blood matter which may be found in the fundal pool can prevent conventional suction devices from properly clearing the pool for purposes of endoscopy.

The flexible portion of an endoscope is first inserted into the gastrointestinal system of a patient. While device 10 can be inserted into a biopsy channel of the endoscope prior to its insertion into the patient, for purposes of this example, distal end 16 of device 10 is inserted and passed through the biopsy channel following the distal end of the endoscope being positioned within the patient's stomach.

To clear the fundal pool, thus enabling an inspection of the obscured stomach lining via an image sensing device positioned within the distal end of the endoscope, distal end 16 is positioned near the fundal pool. Rotary drive source 20 is initiated and brought to an appropriate rotational speed. The rotation of member 28 lyses the blood and blood matter when positioned in contact with the fundal blood pool, thus dissolving that which would ordinarily obstruct a convention suction device.

While an independent suction device may be used to clear the fundal pool once the material therein is lysed, device 10 allows suction of the material/fluid through the rotation of member 12. More specifically, the rotation of coil member 12 with respect to static second member 36 forcibly causes fluid, dissolved tissue, and tissue particles, to be drawn into annular channel 40 and moved proximally. Suction device 38 is initiated to remove that fluid and dissolved tissue pumped to the proximal end 14.

Throughout a clearing operation, the field of view of the endoscope image sensing device is not obstructed by the rotation of member 28. High-speed rotation of member 28 causes effective transparency within the field of view. The dissolving plane is circular, planar, generally normal to the optical axis, and can be located completely within and approximately equal to the optical field of view of the endoscope. The dissolving process zone is fully visible in real time through the optics of the endoscope and may be continuously or intermittently flushed with a fluid to aid visualization. The intensity of the dissolving action may be visually monitored for effectiveness and safety and to allow intensity adjustments to match tissue conditions and the proximity of member 28/tip 22 to surrounding mucosa or stomach lining.

Following proper observation of the stomach lining, or sufficient clearing of the fundal pool, device 10 and/or the endoscope may be withdrawn from the patient.

Figure 7:
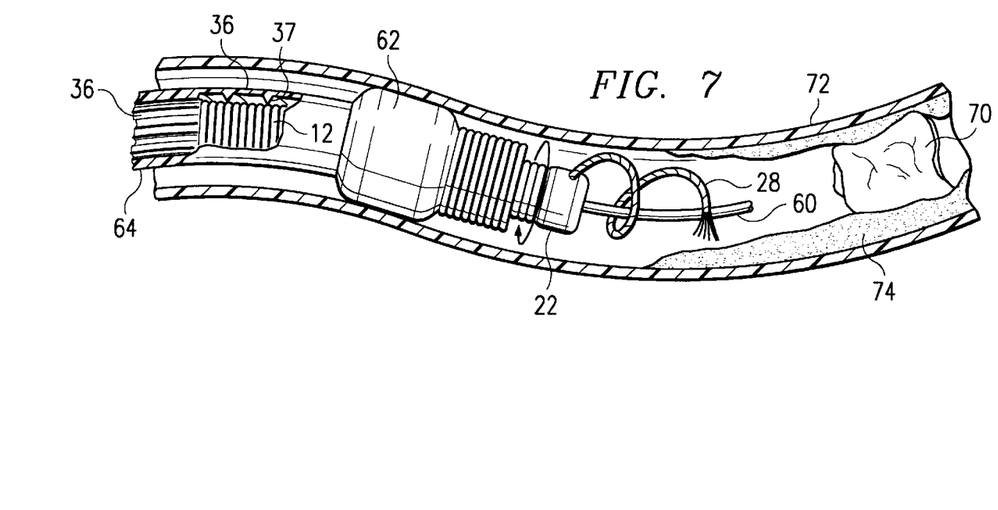
FIG. 7 illustrates an application of yet another embodiment of the mechanical device of the present invention

In reference to FIG. 7, as a thrombotic occlusion removal device, device 10 is inserted into a vascular system via a catheter or a conventional vascular insertion sheath (not shown). The greatest diameter of tip 22 and second member 36 (FIG. 3) is less than approximately 2.0 mm.

Although device 10 may be advanced within a vascular system without the assistance of guide wire 60, the hollow nature of coil member 12 and passage 24 through tip 22 facilitate usage of guide wire 60. Guide wire 60 may be of a conventional design and/or have a radio-opaque tip that could be an enlarged end stop of conventional design for positioning and x-ray visibility, such not being critical to the structure of the present invention.

In operation, device 10 is positioned upstream of vascular obstruction or blockage 70. Care should be taken when positioning guide wire 60 so as not to disrupt vascular obstruction 70, which could prematurely cause vascular obstruction 70, or portions thereof, to flow away from the obstructed site. For the purposes of this example, vascular obstruction 70 is positioned at a narrowing of vessel 72, such narrowing being due to plaque deposits 74 or the like.

To facilitate the safe removal of thrombotic obstruction 70, second member 36 could incorporate sealing balloon 62. In use, once second member 36 is properly positioned, sealing balloon 62 is inflated. The inflated diameter of balloon 62 is greater than the natural diameter of the receiving vessel 72, so as to create a seal, but not of such diameter so as to compromise the integrity of the vessel 72. While inflation of balloon 62 prevents or reduces blood flow through vessel 72, adverse effects associated which the induced ischemia should be no greater than that caused by the thrombotic occlusion 70 given the brief time balloon 62 is to be inflated (for example, 20–30 seconds).

Balloon 62 is a thin membrane, inflation-type balloon which conforms to the outer periphery of second member 36 when uninflated. Balloon 62 is in fluid communication with inflation lumen 64. Inflation lumen 64 opens into the balloon interior and terminates at a proximal end, such proximal end being adapted to be coupled to an inflation device (not shown), for example, a syringe. In another embodiment, a second inflation balloon (not shown) could be provided downstream of thrombotic occlusion 70, thus allowing a lysing operation between balloon 62 and the second inflation balloon.

To lyse thrombotic occlusion 70, coil member 12 is initiated and brought to a desired rotational speed. Coil member 12 can be advanced along guide wire 60 to allow member 28 to come in contact with and enter thrombotic occlusion 70. Member 28 shears thrombotic occlusion 70, thus dissolving the occlusive matter. Unlike known systems which must closely manage the size and the advancement of their "disruption assemblies" to prevent damage to vessel 72 or disturbance of deposits 74, member 28 automatically conforms to the inner diameter of vessel 72/deposits 74.

Rotation of coil member 12 with respect to static second member 36 forcibly causes fluid, tissue particles, and dissolved thrombotic occlusion 70 to be drawn into annular channel 40 and moved proximally. Suction device 38 may be initiated to remove that fluid, particles of tissue, and dissolved matter caused to be pumped to the proximal end 14 as well as to contribute to the suction of fluid/tissue material proximally.

For vascular applications, coil member 12 and tip 22 are preferably constructed of a material which facilitates the observation of device 10 through a fluoroscope when device 10 is in an operative position.

While the invention has been described herein relative to a number of particularized embodiments, it is understood that modifications of, and alternatives to, these embodiments, such modifications and alternatives realizing the advantages and benefits of this invention, will be apparent to those of ordinary skill in the art having reference to this specification and its drawings. It is contemplated that such modifications and alternatives are within the scope of this invention as subsequently claimed herein, and it is intended that the scope of the invention claimed herein be limited only by the broadest interpretation of the appended claims to which the inventors are legally entitled.

What is claimed is:

1. A mechanical device for physically lysing friable/coagulated tissue within a human body, the device comprising a drive member having a proximal end and a distal end, the proximal end being adapted to engage a rotary drive source and the distal end having a filament member extending therefrom, the filament member being suitable to dissolve friable/coagulated material when the drive member is rotated at a speed equal to at least a predetermined rotational speed, wherein, when the drive member is rotated at the predetermined rotational speed, a distal end of the filament member extends distally beyond the distal end of the drive member, and wherein the filament member lacks stiffness and resiliency, and is thereby structurally flaccid.

2. A device in accordance with claim 1, wherein an exterior surface of the drive member defines a substantially helical path between the proximal end and the distal end.

3. A device in accordance with claim 2, further comprising tubing capable of dispensing a fluid positioned within an inner diameter of the drive member and having a proximal end adapted to be coupled to a fluid source.

4. A device in accordance with claim 2, further comprising a flexible member to receive and encompass at least a portion of the drive member.

5. A device in accordance with claim 4, wherein the flexible member is a spiral coil wound in a first direction.

6. A device in accordance with claim 5, wherein the first direction and a spiral direction of the helical path are opposite.

7. A device in accordance with claim 5, wherein the first direction and a spiral direction of the helical path are in a same direction.

8. A device in accordance with claim 4, wherein the flexible member has one or more ridges formed along an inner diameter of the flexible member.

9. A device in accordance with claim 8, wherein the one or more ridges includes a helical ridge.

10. A device in accordance with claim 9, wherein a spiral direction of the helical path and a winding of the helical ridge are in a same direction.

11. A device in accordance with claim 9, wherein a spiral direction of the helical path and a winding of the helical ridge are in an opposite direction.

12. A device in accordance with claim 4, wherein the flexible member has an inflatable sealing balloon positioned at a distal end thereof.

13. A device in accordance with claim 2, wherein the drive member is a coil.

14. A device in accordance with claim 1, wherein the filament member is retractable so that the filament member may be at least partially retracted relative to the distal end of the drive member.

15. A device in accordance with claim 1, wherein the filament member is adapted to at least initially assume a predefined spiral shape.

16. A mechanical device for dissolving friable/coagulated material within a human body, the device comprising:
a rotary drive source;
a first coil member having a proximal end, coupled to the rotary drive source, and a non-abrasive tip, wherein the tip includes at least one non-rigid thread member, extending for a length, that is suitable to dissolve friable/coagulated material through shear when the rotary drive source operates at least at a predetermined rotational speed;

wherein, when the first coil member is rotated at the predetermined rotational speed, the length of the at least one thread member assumes a generally spiral shape, in accordance with a direction of rotation, and a distal end of the at least one thread member extends distally beyond the tip.

17. A lysing device for dissolving friable/coagulated material within a human body, the device comprising a drive member having a proximal end and a distal end, the proximal end being adapted to engage a rotary drive source and the distal end having a lithe thread member extending therefrom, the thread member being without both stiffness and resiliency but being suitable to effect a dissolution of friable/coagulated material positioned distal to the device when the drive member is rotated at least at a predetermined rotational speed.

18. A device in accordance with claim 17, further comprising a second flexible member to receive and encompass at least a portion of the drive member.

19. A device in accordance with claim 18, wherein an exterior surface of the drive member defines a substantially helical path having a first winding, and the second flexible member is a coil having a second winding.

20. A device in accordance with claim 19, wherein the second flexible member has a fluid impermeable membrane about and encompassing its outer surface.

21. A device in accordance with claim 18, wherein the second flexible member has one or more ridges formed along its inner diameter.

22. A device in accordance with claim 21, wherein the one or more ridges includes a helical ridge.

23. A device in accordance with claim 21, wherein the one or more ridges include at least one longitudinal ridge.

24. A device in accordance with claim 18, wherein the second flexible member has an inflatable sealing balloon positioned at a distal end thereof.

25. A device in accordance with claim 18, wherein a proximal end of the second flexible member is adapted to be coupled to a suction device.

26. A device in accordance with claim 17, wherein the thread member is expanded polytetrafluoroethylene.

27. A device in accordance with claim 17, wherein the thread member is at least partially retractable so that the member may be retracted within the flexible member.

28. A mechanical device for physically dissolving friable/coagulated material within a human body, the device comprising:
  a first coil having a proximal end and a distal end, the proximal end being adapted to engage a rotary drive source; and
  a non-abrasive tip, positioned at the distal end of the first coil, having a non-rigid member attached thereto, the member being inherently flaccid but suitable to dissolve friable/coagulated material positioned distally from the tip when the first coil is rotated at a speed at least equal to a predetermined rotational speed.

29. A lysing device for physically dissolving friable/coagulated material within a vessel, the device comprising a flexible member having a proximal end and a distal end, the proximal end being adapted to engage a rotary drive source and the distal end having a lithe filament member extending therefrom, the filament member, having a length and lacking stiffness and resiliency along such length, is suitable to effect a lysing of distally positioned friable/coagulated material through shear when the flexible member is rotated at least at a predetermined rotational speed, wherein, the filament member automatically conforms in an operative state to an inner diameter of the vessel when the inner diameter of the vessel is approximately equal to or less than two times the filament member length.

30. A mechanical device for physically lysing friable/coagulated tissue within a human body, the device comprising a flexible member having a proximal end and a distal end, the proximal end being adapted to engage a rotary drive source and the distal end having at least one lysing member extending therefrom, the at least one lysing member being formed from a high-density, polymer material that is non-resilient and inherently without stiffness.

31. A mechanical device in accordance with claim 30, wherein during operation the at least one lysing member extends distally from the tip of the flexible member to allow lysing of distally positioned friable/coagulated tissue.

32. A mechanical device in accordance with claim 30, wherein the at least one lysing member incorporates an abrasive material.

33. A mechanical device in accordance with claim 30, wherein the at least one lysing member extends distally from the tip of the flexible member to allow lysing of distally positioned friable/coagulated tissue.

34. A device in accordance with claim 30, wherein the filament member is adapted to at least initially assume a predefined spiral shape.

35. A mechanical device for physically lysing friable/coagulated tissue within a human body and removing lysed friable/coagulated tissue, the device comprising:
  a drive member having a proximal end and a distal end and a defined helical path along an exterior surface of the drive member therebetween, the proximal end being adapted to engage a rotary drive source and the distal end having a lysing element, the lysing element being inherently flaccid, without stiffness and resiliency along a length of the lysing element, but suitable to effect a dissolution of friable/coagulated material when the drive member is rotated at a speed equal to at least a predetermined rotational speed; and
  a covering member which encompasses a length of the drive member, wherein the covering member defines at least one fluid travel path along an inner surface.

36. A mechanical device in accordance with claim 35, wherein the at least one fluid travel path is defined by at least one longitudinal ridge extending along at least a portion of the inner surface.

37. A mechanical device in accordance with claim 35, wherein the at least one fluid travel path is defined by at least one helical ridge extending along at least a portion of the inner surface.

38. A mechanical device in accordance with claim 37, wherein a spiral direction of the helical path and a spiral direction by the at least one helical ridge are in a same direction.

39. A mechanical device in accordance with claim 37, wherein a spiral direction of the helical path and a spiral direction by the at least one helical ridge are in different directions.

40. A mechanical device in accordance with claim 35, wherein the covering member is a coil.

41. A lysing device for dissolving friable/coagulated material within a human body, the device comprising a drive member having a proximal end and a distal end, the proximal end being adapted to engage a rotary drive source and the distal end having a lithe thread member extending therefrom, the thread member, being structurally without stiffness and resiliency, incorporates an abrasive material to facilitate the dissolution of friable/coagulated material positioned distal to the device when the drive member is rotated at least at a predetermined rotational speed.

42. A mechanical device for physically lysing friable/coagulated tissue within a human body and removing lysed friable/coagulated tissue, the device comprising:

a first coil member having a proximal end and a distal end and a helical winding there between, the proximal end being adapted to engage a rotary drive source and the distal end having a lysing element, the lysing element being inherently flaccid but suitable to dissolve friable/coagulated material when the drive member is rotated at a speed equal to at least a predetermined rotational speed; and a second coil member which receives and encompasses at least a portion of a length of the first coil member.

43. A method of evacuating a stomach fundal blood pool, comprising the steps of:

providing a dissolution device comprising a drive member having a proximal end and a distal end, the proximal end engaging a rotary drive source and the distal end having a lithe thread member extending therefrom, wherein the thread member is inherently flaccid but suitable to dissolve friable/coagulated material positioned distal to the device when the drive member is rotated at least at a predetermined rotational speed;

providing an endoscope with an insertion portion with at least one work lumen extending therethrough and an imaging device, wherein the work lumen receives the drive member of the dissolution device;

inserting the insertion portion of the endoscope into the stomach of a patient and positioning a distal end of the insertion portion within the blood pool;

initiating the drive source and increasing a rotational speed of the drive source to at least the predetermined rotation speed; and lysing matter within the blood pool to reduce the matter within the blood pool to the certain size to enable evacuation of the blood pool and visualization of the stomach with the imaging device.

44. A method in accordance with claim 43, wherein an exterior surface of the drive member defines a helical path.

45. A method in accordance with claim 43, wherein the drive member is a coil.

46. A method in accordance with claim 43, wherein the dissolution device further includes fluid dispensing tubing, coupled to a fluid source and positioned within an inner diameter of the drive member, and further comprising the step of dispensing matter dissolving fluids into the blood pool.

47. A method in accordance with claim 43, wherein the dissolution device further comprises a coil member encompassing a length of the drive member, forming an annular channel between the coil member and the drive member for the length.

48. A method in accordance with claim 47, wherein the dissolution device further includes fluid dispensing tubing, coupled to a fluid source and positioned within an inner diameter of the drive member, and further comprising the step of dispensing fluid to clear the annular channel during operation of the drive source.

49. A method in accordance with claim 43, wherein the thread member establishes a planar dissolution zone when the drive member is rotated at the at least predetermined rotational speed, and the thread member enables visualization by the imaging device through the planar dissolution zone.

50. A method in accordance with claim 49, wherein the rotational speed of the drive member is variable, and further comprising the step of adjusting the rotational speed of the drive member based on visual information provided by the imaging device of the endoscope.

51. A method of clearing a vascular obstruction, comprising the steps of:

providing a dissolution device comprising a drive member having a proximal end and a distal end, the proximal end engaging a rotary drive source and the distal end having a thread member extending therefrom, wherein the thread member lacks an inherent stiffness and resiliency along its length, and is thereby structurally flaccid, but is suitable to dissolve friable/coagulated material positioned distal to the device when the drive member is rotated at least at a predetermined rotational speed;

providing an insertion and guiding device to receive the second member;

inserting the insertion device into the vascular system of a patient and passing the dissolution device therethrough;

positioning the distal end of the dissolution device in a vessel near a vascular obstruction;

initiating the drive source and increasing a rotational speed of the drive source to at least the predetermined rotation speed; and engaging and lysing the vascular obstruction.

52. A method in accordance with claim 51, wherein the dissolution device further includes a second member, having at least one formed ridge along an interior surface thereof, for encompassing a length of the drive member, the drive member and the second member forming an annular channel therebetween.

53. A method in accordance with claim 52, wherein the drive member and the second member are adapted to draw lysed material and fluid proximally and further dissolve lysed material within the annular channel when the drive member is rotated at least at the predetermined speed.

54. A method in accordance with claim 51, wherein the insertion device includes at least one inflatable balloon at a distal end, and further comprising the step of inflating a first balloon to obstruct the vessel prior to the step of initiating the drive source.

55. A method in accordance with claim 52, wherein the thread member is adapted to assume an initial predefined spiral shape, and prior to increasing the rotational speed of the drive source, further comprising the step of penetrating the obstruction with the thread member.

56. A method in accordance with claim 51, wherein the thread member incorporates an abrasive material.

* * * * *

UNITED STATES PATENT AND TRADEMARK OFFICE
CERTIFICATE OF CORRECTION

PATENT NO : 6,113,614
DATED : September 5, 2000
INVENTOR(S) : Eric L. Mears

It is certified that error appears in the above-identified patent and that said Letters Patent is hereby corrected as shown below:

Column 11, line 44 (claim 27, line 2), after "so that the", insert --thread--.

Column 12, line 26 (claim 34, line 2, delete "filament" and insert --lysing-- .

Column 13, line 13 (claim 42, lines 10 and 11), delete "drive" and insert --first coil-- .

Signed and Sealed this

Fifteenth Day of May, 2001

Attest:

NICHOLAS P. GODICI

Attesting Officer      Acting Director of the United States Patent and Trademark Office